United States Patent
Lukács et al.

(10) Patent No.: US 7,133,140 B2
(45) Date of Patent: Nov. 7, 2006

(54) APPARATUS AND MEASUREMENT PROCEDURE FOR THE FAST, QUANTITATIVE, NON-CONTACT TOPOGRAPHIC INVESTIGATION OF SEMICONDUCTOR WAFERS AND OTHER MIRROR LIKE SURFACES

(75) Inventors: István Endre Lukács, Budapest (HU); János Makai, Budapest (HU); Lothar Pfitzner, Erlangen (DE); Ferenc Riesz, Szentendre (HU); Béla Szentpali, Budapest (HU)

(73) Assignees: Fraunhofer-Gesellschaft zur Foerderung der angewandten Forschung E.V., Munich (DE); Hungarian Academy of Sciences Research Institute for Technical Physics and Materials Science, Budapest (HU)

( * ) Notice: Subject to any disclaimer, the term of this patent is extended or adjusted under 35 U.S.C. 154(b) by 0 days.

(21) Appl. No.: 10/814,252

(22) Filed: Apr. 1, 2004

(65) Prior Publication Data

US 2004/0263864 A1 Dec. 30, 2004

Related U.S. Application Data

(60) Provisional application No. PCT/EP02/11011, filed on Oct. 1, 2002.

(30) Foreign Application Priority Data

Oct. 2, 2001 (HU) .................................... 0104057

(51) Int. Cl.
*G01B 11/24* (2006.01)
(52) U.S. Cl. ................... 356/612; 356/601; 250/492.1; 359/212

(58) Field of Classification Search ........ 356/601–622, 356/310; 250/492.1, 492.2; 359/212, 196, 359/742, 868
See application file for complete search history.

(56) References Cited

U.S. PATENT DOCUMENTS 4,547,073 A * 10/1985 Kugimiya .................. 356/613

(Continued)

FOREIGN PATENT DOCUMENTS

GB 2248500 4/1992

(Continued)

OTHER PUBLICATIONS

Yang, "An Optical Imaging Method for Wafer Warpage Measurements," *Journal of the Electrochemical Society*, vol. 132, No. 5, pp. 1214-1218 (1985).

(Continued)

*Primary Examiner*—Gregory J. Toatley, Jr.
*Assistant Examiner*—Sang H. Nguyen
(74) *Attorney, Agent, or Firm*—Greenblum & Bernstein, P.L.C.

(57) ABSTRACT

Apparatus and process for fast, quantitative, non-contact topographic investigation of samples. Apparatus includes a light source, and a collimating concave mirror structured and arranged to produce a parallel beam and to direct the parallel beam to a sample to be investigated. A structured mask is located between the light source and the concave mirror, and an image sensor structured and arranged to receive a beam reflected from the sample and the concave mirror. Relative positions of the mask and the sensor to other elements of the apparatus are chosen to provide an essentially sharp image of the mask on the sensor. The instant abstract is neither intended to define the invention disclosed in this specification nor intended to limit the scope of the invention in any way.

30 Claims, 2 Drawing Sheets

U.S. PATENT DOCUMENTS

| | | | | |
|---|---|---|---|---|
| 4,568,186 | A | * | 2/1986 | Yoshimura et al. .......... 356/308 |
| 4,705,940 | A | * | 11/1987 | Kohno ........................ 355/55 |
| 4,867,570 | A | * | 9/1989 | Sorimachi et al. ........... 356/603 |
| 4,983,039 | A | * | 1/1991 | Harada et al. ............... 356/328 |
| 5,018,867 | A | * | 5/1991 | Piironen ..................... 356/445 |
| 5,225,890 | A | * | 7/1993 | Lee et al. .................... 356/613 |
| 5,255,116 | A | * | 10/1993 | Araki et al. ................. 359/212 |
| 5,369,489 | A | | 11/1994 | Somekh |
| 5,512,759 | A | * | 4/1996 | Sweatt ..................... 250/492.1 |
| 5,627,639 | A | * | 5/1997 | Mende et al. ................ 356/310 |
| 5,696,581 | A | * | 12/1997 | Kubota et al. ............ 356/124.5 |
| 6,922,482 | B1 | | 7/2005 | Ben-Porath |

FOREIGN PATENT DOCUMENTS

| | | |
|---|---|---|
| WO | 02/29835 | 5/2000 |

OTHER PUBLICATIONS

"Optical Shop Testing," ed. Malacara, John Wiley & Sons, New York pp. 323-349 (1979).

Riesz, "Geometrical Optical Model of the Image Formation in Makyoh (Magic Mirror) Topography," *J.Phys.D: Appl. Phys.*, vol. 33, pp. 3033-3040, XP002229672 UK (2000).

Riesz, "Camera Length and Field of View in Makyoh-topography Instruments," *R.S.I.*, vol. 72, No. 2, pp. 1591-1593, XP002229673 America (Feb 2001).

Reisz, "Makyoh Topography for the Morphological Study of Compound Semiconductor Wafer and Structures," *Material Science & Engineering*, vol. B80, pp. 220-223, XP002229676 NL (2001).

Szabo et al., "Makyoh Topography: Curvature Measurements and Implications for the Image Formation," *Jpn. J. Appl. Phys.*, vol. 35, pp. L258-L261, XP002229674 (Feb. 15, 1999).

Laczik, "Quantitative Makyoh Topography," *Proc. Annual ACM Symp. On Principles of Distributed Computing*, vol. 3743, pp. 151-156, XP000874538 (May 1999).

Török et al., "Applications of Scanning Optical Microscopy in Materials Science to Detect Bulk Microdefects in Semiconductors," *Journal of Microscopy*, vol. 188, No. 1, pp. 1-16, XP002229675 UK (Oct. 1997).

Koehler, "Plane-wave X-ray Topography and its Application to Semiconductor Problems," *Journal of Materials Science*, Material in Electronics, Chapman and Hall, London GB, pp. 167-174, XP000912483, ISSN: 0957-4522 (May 3, 1999).

Kayaalp et al., "Using SEM Stereo to Extract Semiconductor Wafer Pattern Topography," *Proceedings of the SPIE*, SPIE, Bellingham VA, US, vol. 775, pp. 18-26, XP000918713 (1987).

English Language abstract of JP 2001-1135692.

English Language abstract of JP 10-300685.

www.hologenix.com.

* cited by examiner

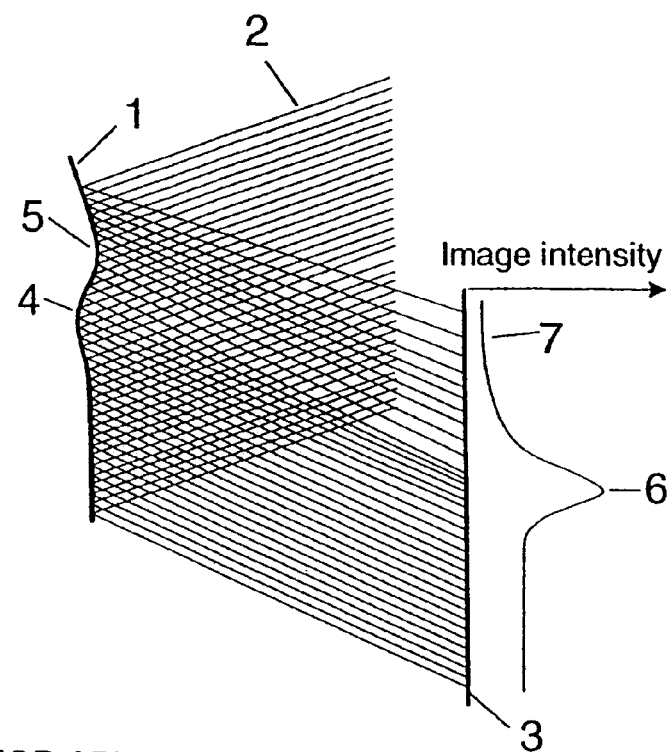
PRIOR ART  Figure 1
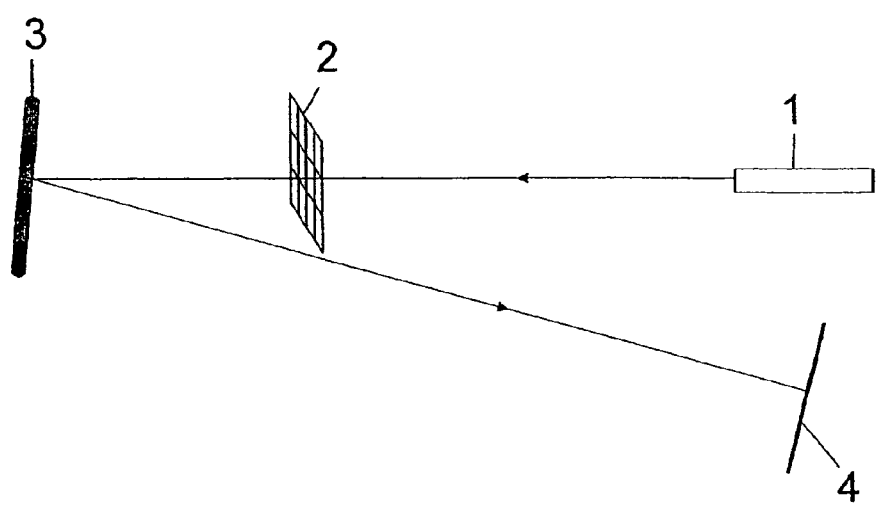
PRIOR ART  Figure 2

APPARATUS AND MEASUREMENT PROCEDURE FOR THE FAST, QUANTITATIVE, NON-CONTACT TOPOGRAPHIC INVESTIGATION OF SEMICONDUCTOR WAFERS AND OTHER MIRROR LIKE SURFACES

CROSS-REFERENCE TO RELATED APPLICATIONS

The present application is a continuation of International Patent Application No. PCT/EP02/11011 filed Oct. 1, 2002, the disclosure of which is expressly incorporated by reference herein in its entirety. The instant application further claims priority Hungarian Patent Application No. 0104057 filed Oct. 2, 2001.

BACKGROUND OF THE INVENTION

1. Field of the Invention

The present invention is directed to an apparatus and process for fast, quantitative, non-contact topographic investigation of semiconductor wafers.

2. Discussion of Background Information

The microelectronics industry requires perfectly flat, mirror like surfaces having defect-free single-crystal wafers as a base for the production of integrated circuits and components. Any deviation from the ideal plane makes the manufacturing process difficult or even impossible or decreases the yield of the manufactured circuits. Such defects may often originate during the individual steps of the crystal and wafer production (cutting, polishing). Many of the technological phases of the production of the integrated circuits (annealing, layer deposition, patterning) may cause curving or warp of the originally flat surface. Consequently, the investigation of the flatness is crucial both for the wafer manufacturer and the consumer. Having a suitable investigating procedure, the wafers can be screened before using them, thus sparing many expensive technological steps. Not only the microelectronics industry requires the investigation of the mirror like surfaces; similar requirements have to be met for optical components, for some precision mechanical parts, as well as for the optical and magnetic disks of the IT industry. The investigating procedure requires high speed, non-contact operation, ability to investigate large-area (diam. >300 mm) samples, high sensitivity, and high lateral resolution (~mm).

The requirement of the non-contact operation is met mainly by optical devices. In practice, the scanning laser beam and the interferometric methods are used. The scanning laser beam procedure uses a small-diameter parallel laser beam that scans the surface and from the position of the reflected laser beam the surface gradient of the actual surface point is determined, providing the surface topography. The disadvantage of the technique is its low speed, high cost and the need for high precision alignments. The interferometric procedures can measure only small-area surfaces.

A different principle is applied in the magic mirror technique (also called "Makyoh topography," see, e.g., U.S. Pat. No. 4,547,073). This technique is depicted in prior art FIG. 1, and the principle of image formation is that a homogeneous parallel beam 2 falls on a surface 1 to be investigated. If the surface is perfectly flat, then a homogeneous spot appears on screen 3 positioned a certain distance away from surface 1. If surface 1 is not uniformly flat, the parallelism of the reflected beam is disturbed causing non-uniformity in its intensity distribution and an image appears on screen 3 that reflects the topography of surface 1. For example, a dent 4 focuses beam 2 causing an intensity maximum 6 on screen 3, while a hillock 5 defocuses beam 2 resulting in an intensity minimum 7. The sensitivity of the technique increases with increasing sample-screen distance. In practice, this basic set-up can be replaced by other, optically equivalent set-ups. For example, the collimated beam can advantageously be produced by a point source located in the focal point of a lens or a concave mirror. The beam reflected from the sample can pass through the lens or can be reflected from the concave mirror and the image can appear on a CCD camera. With suitable set-up, the sensitivity of this method meets the strictest requirements of the semiconductor industry, e.g., detection of a 0.05 µm deep surface dent over a 0.5 mm distance has been reported. However, the disadvantage of this method is the lack of the quantitative evaluation.

International Publication No. WO 00/29835 discloses a completed set-up, as described above, by taking two pictures at two different sample-screen distances; the surface topography and reflectivity map was determined by the iteration of the diffraction integrals of the surface. The method can provide quantitative results, but the disadvantage is the extreme slowness of the algorithm and the high requirements concerning the quality of the beam and the mechanical adjustments.

Prior art FIG. 2 illustrates a set-up described that is similar to the magic mirror arrangement [see K. H. Yang, Journal of the Electrochemical Society, Vol. 132. p. 1214. 1985]. In this set up, a light beam collimated by a collimator 1 falls to surface 3 and a reflected image is formed on screen 4 located some distance away from surface 3. The illuminating beam 1 traverses a quadratic grid 2, and from the position of the image of the grid points, a suitable algorithm calculates the curvature of the surface. The reported evaluation method is suitable only to determine uniform curvatures. A further disadvantage is that, as a consequence of the great grid-sample and grid-screen distances, the diffraction effects cause blurring of the image of the grid, which results in an inaccurate determination of the grid points. Thus, the error of the method increases. Moreover, greater deformation may cause an overlap of the image of the grid points that inhibits evaluation, and limits the density of the grid points decreasing the achievable lateral resolution. The non-normal incident angle causes additional distortions. Another serious disadvantage is the great size of the set-up (several meters).

The Hartman test is known for the evaluation of optical components, especially astronomic mirrors of large diameter, by projected masks [see Optical shop testing, ed. D. Malacara, John Wiley and Sons, New York, 1978, p. 323.] A typical realization of the technique is shown in prior art FIG. 3, in which the light of point source 1 is projected to surface 3 to be investigated through a mask 2, which is an opaque plate with holes, and the beam reflected through the holes reaches screen 4. From the position of the reflected beam of a given (x,y) point on screen 3, the height of the point h(x,y) compared to a reference point having an arbitrarily chosen height of zero, can be calculated by the summation approximation of an integral where the summation is carried out between the reference and the given point on the route defined by the neighboring holes of mask 2. The members of the summation are the product of three quantities: a geometrical constant characteristic to the optical lay-out, the difference of the measured coordinates of the ideally flat and the real surface, and the distance between the given and the neighboring points. For example, for quadratic grids the calculation can be carried out by the equation:

$$h(x, y) = \frac{1}{2L} \sum_i [\Delta x(x'_i - f_{xi}) + \Delta y(y'_i - f_{yi})]$$

where L is the geometric constant, Δx and Δy are the lengths of the grid projected on the sample surface, (fxi, fyi) are the measured coordinates of the image of the surface point ($x_i$, $y_i$) and ($x_i'$, $y_i'$) are the coordinates of the image of the point ($x_i$, $y_i$) for an ideal flat surface. In the practice, more accurate but essentially not different integral approximations can be used.

SUMMARY OF THE INVENTION

The present invention provides a measurement set-up for the non-contact, fast quantitative topographic investigation of semiconductor wafers and other mirror-like surfaces.

According to the instant invention, an apparatus for fast, quantitative, non-contact topographic investigation of samples, includes a light source, and a collimating concave mirror structured and arranged to produce a parallel beam and to direct the parallel beam to a sample to be investigated. A structured mask is located between the light source and the concave mirror, and an image sensor structured and arranged to receive a beam reflected from the sample and the concave mirror. Relative positions of the mask and the sensor to other elements of the apparatus are chosen to provide an essentially sharp image of the mask on the sensor.

In accordance with a feature of the invention, the samples can include semiconductor wafers and other mirror-like surfaces.

According to another feature of the instant invention, the light source may include substantially a point source.

Further, the concave mirror can include an off-axis parabolic mirror.

In accordance with still another feature of the invention, the structured mask may include a quadratic grid.

According to a further feature, the image sensor can include a CCD image sensor.

Moreover, the apparatus can include a converging lens positioned in front of the light source to be in a beam path.

Further, the light source can include a laser and a converging lens structured and arranged to provide a diverging beam.

The light source can include a laser with a built-in converging lens that is structured to provide a diverging beam.

Further, one of a converging and a diverging lens can be positioned in front of the sensor to be in a beam path.

According to the invention, at least one flat mirror can be positioned between the light source and the concave mirror to fold an optical path. At least one of the at least one mirror can be a partially transmitting mirror. Further, at least one of the at least one mirror may be a semi-transparent mirror.

In accordance with another feature of the invention, at least one flat mirror may be positioned between the sample and the concave mirror to fold an optical path. At least one of the at least one mirror can be a partially transmitting mirror. Moreover, at least one of the at least one mirror may be a semi-transparent mirror.

Still further, at least one flat mirror can be positioned between the sensor and the concave mirror to fold an optical path. At least one of the at least one mirror may include a partially transmitting mirror. Further, at least one of the at least one mirror can include a semi-transparent mirror.

According to a still further feature of the present invention, a computer can be coupled to the sensor, and the computer may include an algorithm to calculate a height of a given point of the sample from a position of an image point on the sensor.

The invention is directed to a process for fast, quantitative, non-contact topographic investigation of a sample in the above-noted apparatus. Further, the process can include calculating the height of a given point of the sample from a position of an image point on the sensor.

The present invention is directed to a process for fast, quantitative, non-contact topographic investigation of samples. The process includes directing light through a structured mask onto a concave mirror, directing collimated light to a sample to be investigated, receiving a beam reflected from the sample and the concave mirror, and positioning the mask and the sensor in relation to the mirror and the sample to provide an essentially sharp image of the mask on the sensor.

According to the invention, the process investigates samples that can include semiconductor wafers and other mirror-like surfaces.

In accordance with the instant process, a light source is arranged to produce light.

According to a feature of the process, the concave mirror can include an off-axis parabolic mirror.

Further, according to the process, the structured mask may include a quadratic grid.

In accordance with still another feature of the process, the image sensor can include a CCD image sensor.

The process can also include converging the beam before the mask.

In accordance with still yet another feature of the present invention, the process can include folding an optical path between the sample and the mirror.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows in reference to the noted plurality of drawings by way of non-limiting examples of exemplary embodiments of the present invention, in which like reference numerals represent similar parts throughout the several views of the drawings, and wherein:

FIG. 1 illustrates a prior art scheme of the image formation of a magic-mirror surface examining apparatus;

FIG. 2 illustrates the prior art surface examining apparatus of Yang;

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 3:
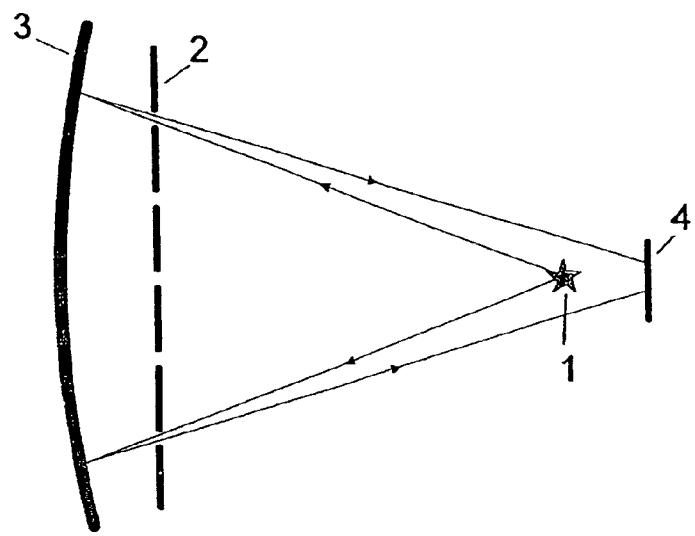
FIG. 3 illustrates the prior art optical lay-out of the Hartmann-test method.
Figure 4:
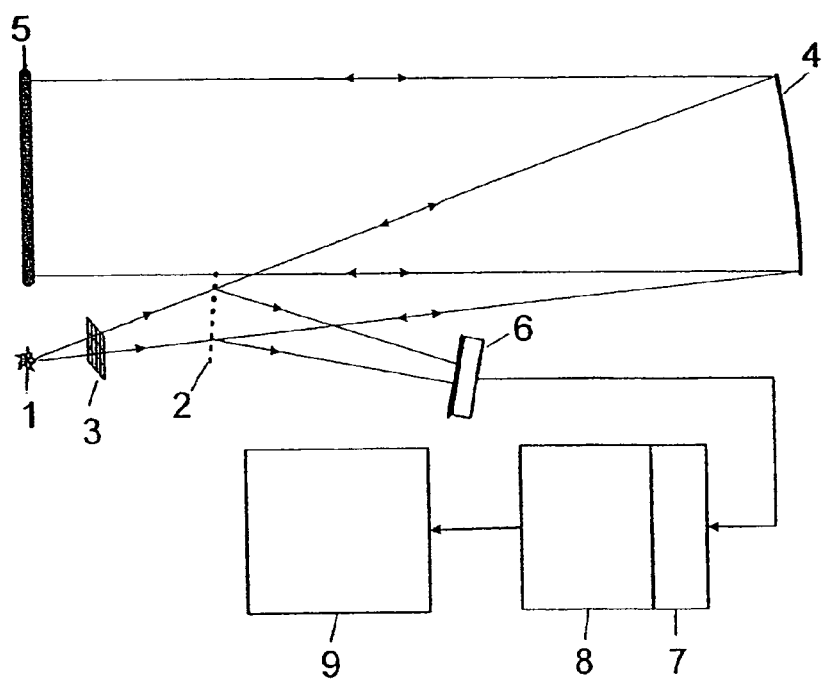
FIG. 4 illustrates a preferred embodiment for the measurement set-up in accordance with the features of the present invention.

The present invention provides a measurement set-up for the non-contact, fast quantitative topographic investigation of semiconductor wafers and other mirror-like surfaces, as illustrated in FIG. 4. The set-up includes an essentially point light source 1, a concave mirror 4 that makes the beam of the light source parallel and projects the collimated light beam onto a studied surface 5. A structured pattern mask 3 is situated between light source 1 and mirror 4, and an image sensor 6 is situated in the path of the light beam reflected from mirror 4. A computer 8 is connected through an appropriate interface 7 to sensor 6 to visualize or produce the image sensed by sensor 6 on a monitor 9 connected to it. Further, computer 8, with a suitable algorithm (e.g., a correlation method), determines the position of the image elements of the mask's image.

The instant invention also provides a measurement procedure, which determines the surface topography of semiconductor wafers and other mirror-like surfaces from the coordinates of the image elements described above and from the coordinates of the image elements of a flat reference surface via the set-up described above and the algorithm of the Hartmann test described above. According to the invention, the positions of mask 3 and image sensor 6 are chosen in such a way that an essentially sharp image of mask 3 is formed on the sensor surface. Thus, the accuracy of the determination of the mask's image elements and, consequently, the accuracy, lateral resolution and dynamic range of the measurement procedure is markedly improved.

In an alternative embodiment of the present invention, a collimating lens can be placed in front of light source 1, i.e., in its optical path, so that this lens makes the light beam emitted by light source 1 less divergent. In this manner, light source 1 can be placed closer to mask 3, such that the size of the measurement apparatus can be decreased.

In an alternative embodiment of the inventions a laser light whose source is made divergent by a converging lens can be utilized in place of light source 1.

In another alternative embodiment of the invention, a converging or diverging lens can be placed in front of image sensor 6. In this way, an appropriate magnification and sensitivity can be set-up.

In a further alternative embodiment of the invention, the light path enclosed by image sensor 6 and studied surface 5 or the light path enclosed by light source 1, studied surface 5 and situated on either side of mask 3 is folded by one or more plane mirrors. These mirrors can include one or more semi-transparent mirrors. In accordance with this embodiment, the size of the measurement set-up can be decreased.

In the exemplary embodiment of FIG. 4, concave mirror 4 is an off-axis parabolic mirror, in whose focal point the point light source is situated. The advantage of the off-axis parabolic mirror is that the respective light paths are perpendicular to the surface of mask 2, to studied surface 5, and to image sensor 6. Thus, the errors associated with the non-normal light incidence of previous set-ups are decreased. Another advantage of the off-axis parabolic mirror over to spherical mirrors and lenses is the lack of optical aberrations. According to the invention, it is advantageous if, in the exemplary embodiment of the invention, the light beam reflected first from studied surface 5 and then from concave mirror 4 is projected onto the surface of image sensor 6 by a semi-transparent mirror.

Moreover, it is understood that the embodiments described above can be combined with each other without departing from the spirit and scope of the instant invention.

Further, the instant invention provides advantages over the above-discussed earlier solutions, in that the instant invention is suitable for the fast (in practice, real-time), quantitative, automated, reproducible determination of the surface topography, and lateral resolution is improved.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. An apparatus for fast, quantitative, non-contact topographic investigation of samples, comprising:
   a light source;
   a collimating concave mirror structured and arranged to produce a parallel beam and to direct the parallel beam to a sample to be investigated;
   a structured mask located between said light source and said concave mirror; and
   an image sensor structured and arranged to receive a beam reflected from the sample and said concave mirror, wherein relative positions of said mask and said sensor to other elements of the apparatus are chosen to provide an essentially sharp image of the mask on the sensor.

2. The apparatus in accordance with claim 1, wherein the samples comprise semiconductor wafers and other mirror-like surfaces.

3. The apparatus in accordance with claim 1, wherein said light source comprises substantially a point source.

4. The apparatus in accordance with claim 1, wherein said concave mirror comprises an off-axis parabolic mirror.

5. The apparatus in accordance with claim 1, wherein said structured mask comprises a quadratic grid.

6. The apparatus in accordance with claim 1, wherein said image sensor comprises a CCD image sensor.

7. The apparatus in accordance with claim 1, further comprising a converging lens positioned in front of said light source to be in a beam path.

8. The apparatus in accordance with claim 1, wherein said light source comprises a laser and a converging lens structured and arranged to provide a, diverging beam.

9. The apparatus in accordance with claim 1, wherein said light source comprises a laser with a built-in converging lens that is structured to provide a diverging beam.

10. The apparatus in accordance with claim 1, further comprising one of a converging and a diverging lens positioned in front of said sensor to be in a beam path.

11. The apparatus in accordance with claim 1, wherein at least one flat mirror is positioned between said light source and said concave mirror to fold an optical path.

12. The apparatus in accordance with claim 11, wherein at least one of said at least one mirror comprises a partially transmitting mirror.

13. The apparatus in accordance with claim 11, wherein at least one of the at least one mirror is a semi-transparent mirror.

14. The apparatus in accordance with claim 1, wherein at least one flat mirror is positioned between the sample and said concave mirror to fold an optical path.

15. The apparatus in accordance with claim 14, wherein at least one of said at least one mirror comprises a partially transmitting mirror.

16. The apparatus in accordance with claim 14, wherein at least one of said at least one mirror comprises a semi-transparent mirror.

17. The apparatus in accordance with claim 1, wherein at least one flat mirror is positioned between said sensor and said concave mirror to fold an optical path.

18. The apparatus in accordance with claim 17, wherein at least one of said at least one mirror comprises a partially transmitting mirror.

19. The apparatus in accordance with claim 17, wherein at least one of said at least one mirror comprises a semi-transparent mirror.

20. The apparatus in accordance with claim 1, further comprising a computer coupled to said sensor, said computer comprising an algorithm to calculate a height of a given point of the sample from a position of an image point on said sensor.

21. A process for fast, quantitative, non-contact topographic, investigation of a sample in the apparatus in accordance with claim 1.

22. The process in accordance with claim 21, further comprising calculating the height of a given point of the sample from a position of an image point on the sensor.

23. A process for fast, quantitative, non-contact topographic investigation of samples, comprising:
    directing light through a structured mask onto a concave mirror;
    directing collimated light to a sample to be investigated; and
    receiving a beam reflected from the sample and the concave mirror; and
    positioning the mask and the sensor in relation to the mirror and the sample to provide an essentially sharp image of the mask on the sensor.

24. The process in accordance with claim 23, wherein the samples comprise semiconductor wafers and other mirror-like surfaces.

25. The process in accordance with claim 23, wherein a light source is arranged to produce light.

26. The process in accordance with claim 23, wherein the concave mirror comprises an off-axis parabolic mirror.

27. The process in accordance with claim 23, wherein the structured mask comprises a quadratic grid.

28. The process in accordance with claim 23, wherein the image sensor comprises a CCD image sensor.

29. The process in accordance with claim 23, further comprising converging the beam before the mask.

30. The process in accordance with claim 23, further comprising folding an optical path between the sample and the mirror.

* * * * *